United States Patent
Hecht

(10) Patent No.: US 6,871,993 B2
(45) Date of Patent: Mar. 29, 2005

(54) INTEGRATING LED ILLUMINATION SYSTEM FOR MACHINE VISION SYSTEMS

(75) Inventor: Kurt Hecht, Hartsville, PA (US)

(73) Assignee: Accu-Sort Systems, Inc., Hatfield, PA (US)

(*) Notice: Subject to any disclaimer, the term of this patent is extended or adjusted under 35 U.S.C. 154(b) by 47 days.

(21) Appl. No.: 10/186,798

(22) Filed: Jul. 1, 2002

(65) Prior Publication Data

US 2004/0001344 A1 Jan. 1, 2004

(51) Int. Cl.[7] .............................................. F21V 7/04
(52) U.S. Cl. ..................... 362/555; 362/241; 362/244; 362/245; 362/247; 362/294; 362/373; 362/345
(58) Field of Search ................................. 362/241, 247, 362/244, 245, 345, 555, 249, 373, 294

(56) References Cited

U.S. PATENT DOCUMENTS

| | | | | |
|---|---|---|---|---|
| 4,587,601 A | * | 5/1986 | Collins | 362/235 |
| 4,617,619 A | * | 10/1986 | Gehly | 362/804 |
| 4,651,257 A | * | 3/1987 | Gehly | 362/33 |
| 4,755,916 A | * | 7/1988 | Collins | 362/236 |
| 5,272,607 A | * | 12/1993 | Grimm | 362/219 |
| 5,291,009 A | | 3/1994 | Roustaei | |
| 5,349,172 A | | 9/1994 | Roustaei | |
| 5,359,185 A | | 10/1994 | Hanson | |
| 5,430,285 A | | 7/1995 | Karpen et al. | |
| 5,449,892 A | | 9/1995 | Yamada | |
| 5,475,208 A | | 12/1995 | Marom | |
| 5,585,616 A | | 12/1996 | Roxby et al. | |
| 5,623,137 A | | 4/1997 | Powers et al. | |
| 5,838,247 A | * | 11/1998 | Bladowski | 340/815.45 |
| 5,857,767 A | * | 1/1999 | Hochstein | 362/294 |
| 5,924,785 A | * | 7/1999 | Zhang et al. | 362/241 |
| 6,238,073 B1 | * | 5/2001 | Ito et al. | 362/544 |
| 6,471,371 B1 | * | 10/2002 | Kawashima et al. | 362/235 |
| 6,474,852 B1 | * | 11/2002 | Ohkohdo et al. | 362/487 |

* cited by examiner

Primary Examiner—Thomas M. Sember
Assistant Examiner—Jacob Y. Choi
(74) Attorney, Agent, or Firm—Volpe and Koenig, P.C.

(57) ABSTRACT

A system for focusing light on an illumination area. The system includes a reflector having a focusing reflective surface and a focal region and an LED array having a plurality of LEDs located within the focal region. Each of the plurality of LEDs in the LED array is positioned to emit light toward the focusing reflective surface. The focusing reflective surface reflects light from each of the plurality of LEDs of the LED array toward the illumination area.

13 Claims, 3 Drawing Sheets

INTEGRATING LED ILLUMINATION SYSTEM FOR MACHINE VISION SYSTEMS

BACKGROUND

The present invention relates to an illumination system for use with machine vision systems, such as optical and barcode scanning systems. More particularly, it relates to a system for focusing light on a line or area in which a machine vision system collects image data.

In order to increase accuracy and maintain consistency in the data collected by machine vision systems it is important to have a direct source of light to fully illuminate the area being scanned (hereinafter the "illumination area"). In the case of a linear scanner, a narrow illumination line is sufficient. For area-array based scanning equipment such as video cameras, it is necessary to illuminate a wider area. As used in this application and the appended claims, the term "illumination area" should be understood as including both area and line illumination. Such illumination systems have traditionally consisted of either direct illumination or a combination of direct and reflected illumination, in which light energy is focused onto an illumination area using a reflector. Systems using a combination of direct and reflected light typically use incandescent or HID light sources. Such systems are not ideal because they are somewhat inefficient in that they consume energy at a relatively high rate and generate a large amount of heat.

SUMMARY

The present invention comprises a system for efficiently focusing light onto an illumination area. The system includes a reflector having a focusing reflective surface with a focal region, and an LED array comprising a plurality of LEDs located within the focal region. Each of the plurality of LEDs is positioned to emit light toward the focusing reflective surface. The focusing reflective surface reflects light from each of the plurality of LEDs of the LED array toward the illumination area.

In another respect, the present invention comprises a system for focusing light onto an illumination area. The system includes a reflector having a focusing reflecting surface and a focal region. A core to dissipate heat having a mounting surface oriented toward the focusing reflected surface is also provided. A substrate is located within the focal region and secured to the mounting surface such that it faces toward the reflector. A first LED array is provided and comprises a plurality of LEDs which are indirectly surface mounted on the substrate and positioned to emit light in the direction of the focusing reflective surface. The focusing reflective surface reflects light from each of the plurality of the LEDs toward the illumination area.

BRIEF DESCRIPTION OF THE DRAWING(S)

The foregoing summary, as well as the following detailed description of the invention, will be better understood when read in conjunction with the appended drawings. For the purpose of illustrating the invention, presently preferred embodiments are shown in the drawings. It should be understood, however, that the invention is not limited to the precise arrangements and instrumentalities shown. In the drawings.

DETAILED DESCRIPTION OF THE PREFERRED EMBODIMENT(S)

Figure 1:
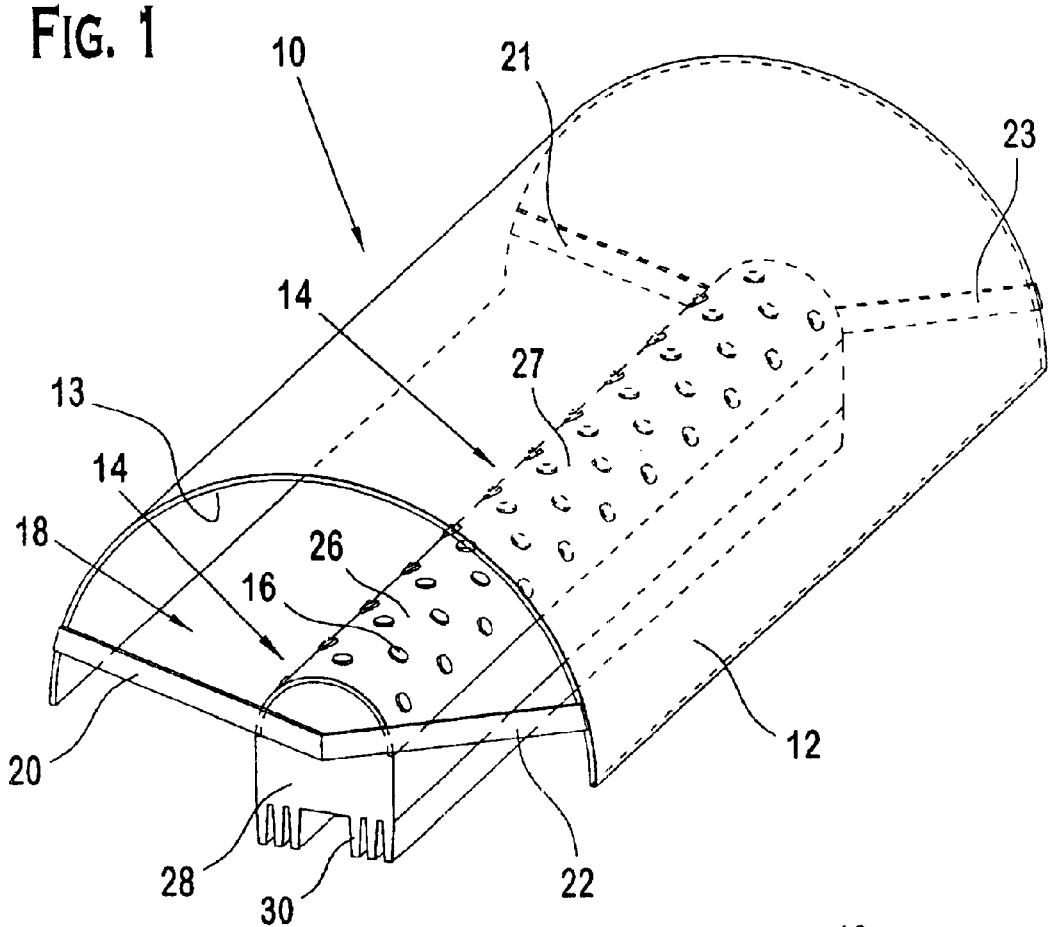
FIG. 1 is a top perspective view showing a first embodiment of the illumination system of the present invention, which is designed for use with linear scanning systems.
Figure 2:
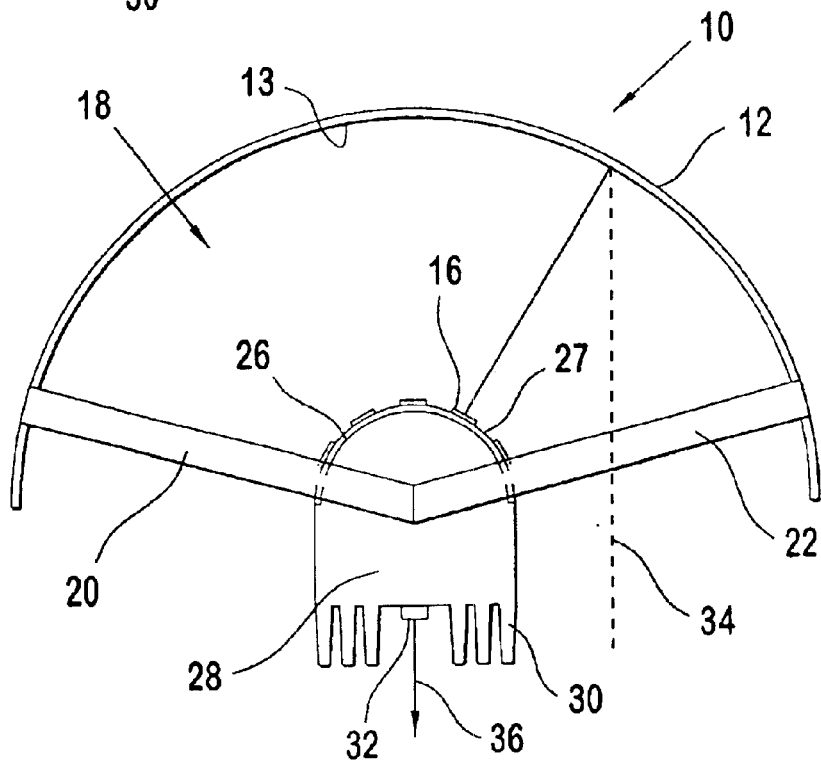
FIG. 2 is an end view of the illumination system of FIG. 1.
Figure 3:
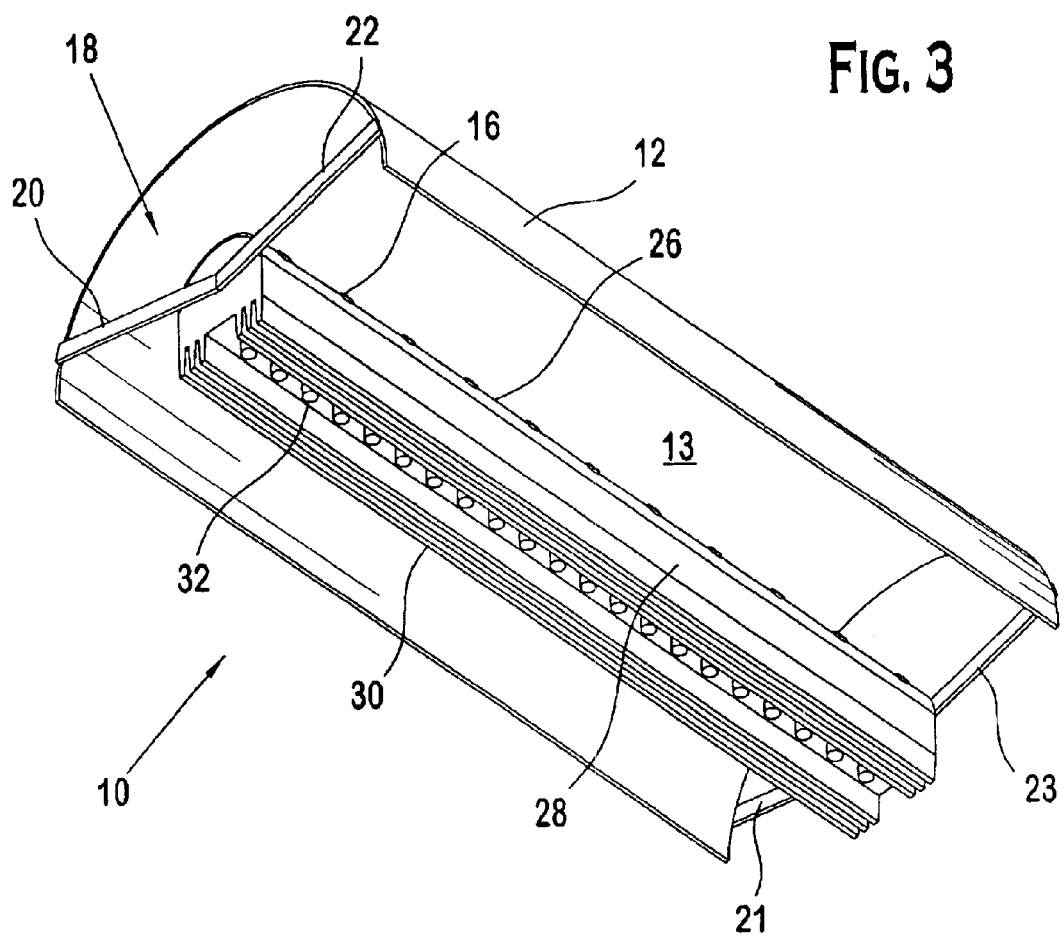
FIG. 3 is a bottom perspective view of the illumination system of FIG. 1.

Referring now to FIGS. 1–3, reference numeral 10 refers generally to an illumination system in accordance with the present invention. The system 10 comprises a reflector 12 and an LED array 14 and is best suited for linear scanning systems because it generates a slender, elongated illumination area.

The reflector 12 includes a focusing reflective surface 13 that is concave in shape. An elliptical cross-sectional shape is preferred, but other shapes, such as parabolic and hyperbolic could be used, for example. The reflector 12 can be formed of any suitable reflective material. The preferred shape of the reflective surface 13 would vary depending upon the application in which the system 10 is being used. Factors determining the preferred shape include the desired light beam thickness and operating range, for example.

The LED array 14 comprises a plurality of surface mounted LEDs 16 that are arranged to emit light energy (shown schematically as line 34) toward the reflective surface 13. The LEDs 16 preferably have zero power lenses. The relative arrangement, spacing and intensity of the LEDs 16 would, of course, depend upon the desired profile of the illumination area and the intensity of light.

In the first preferred embodiment, the LEDs 16 are surface mounted on a substrate 26, which preferably comprises a flexible printed circuit board ("PCB") and can also be formed from several rigid PCBs that are interconnected. The substrate 26 provides a surface for supporting the LEDs 16, as well as a means for providing drive current to the LEDs 16. The substrate 26 is thermally secured to a mounting surface 29 of a aluminum core 28 and preferably forms a convex outer surface 27 when mounted. The core can be made of any suitable thermally conductive and rigid material, such as aluminum, and is included to provide a controlled surface contour for mounting of the substrate 26 and to dissipate heat. In that respect, the core 28 preferably includes heat sink fins 30. Optionally, the core 28 may incorporate active heat dissipation systems, such as liquid cooling passages that can be connected to a cooling system or fans providing forced air cooling, to remove heat generated by the LEDs 16 and the substrate 26 to allow for higher power operating levels.

The core 28 and substrate 26 are preferably positioned so that all of the LEDs 16 are located within the focal region 18 of the reflective surface 13. The position of the core 28 may be fixed relative to the reflector 12 by any convenient means, such as brackets 20, 21, 22, 23, for example. In the embodiment shown in FIGS. 1–3, the focal region 18 is located roughly in the area bounded by the brackets 20, 21, 22, 23 and the reflective surface 13. The shape of the focal region 18 of alternative embodiments would, of course, vary according to the shape of the reflective surface 13.

Optionally, as shown in FIGS. 2 and 3, the core 28 may also include a plurality of downward-facing LEDs 32, which emit light energy (shown schematically as line 36) directly toward the illumination area. The downward-facing LEDs 32 may each optionally include a built-in focusing lens to better focus the light energy onto the illumination area. Alternatively, a separate cylindrically-shaped focusing lens could be used (see focusing lens 133 in FIG. 4).

Figure 4:
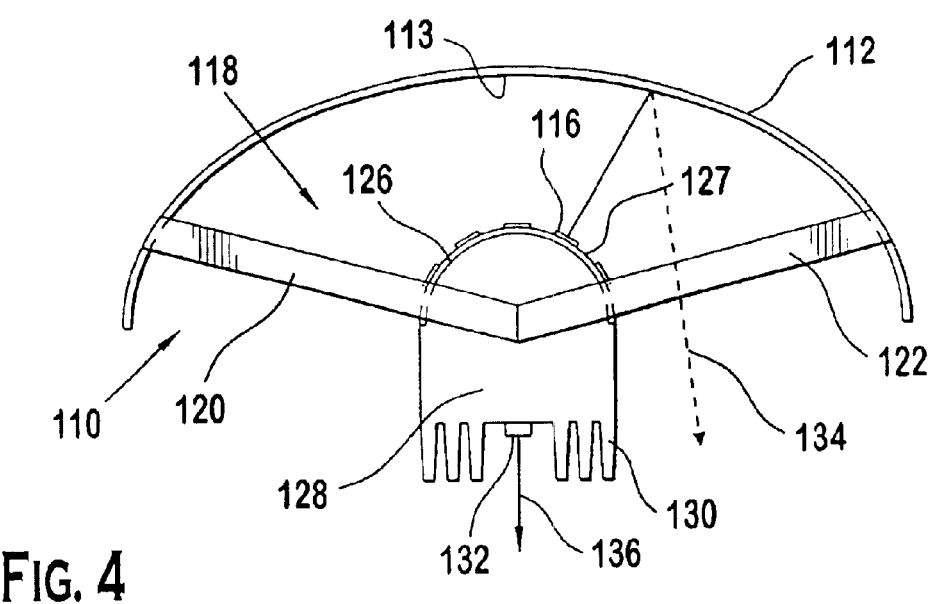
FIG. 4 is an end view of a first alternative embodiment of the scanning system shown in FIGS. 1–3.

FIG. 4 shows a first alternative embodiment of the present invention in which like elements in this embodiment are represented by reference numerals increased by factors of 100 (for example the reflector 12 in FIG. 1 corresponds to the reflector 112 in FIG. 4). FIG. 4 shows an illumination system 110 having a reflective surface 113, which is hyberbolic or elliptical, that has a flatter cross-sectional shape than the embodiment shown in FIGS. 1–3. This alternative shape provides a wider illumination area than the system 10 of the first embodiment. As discussed above, FIG. 4 shows an optional cylindrically-shaped focusing lens 133 located below the downward-facing LEDs 132 to better focus the light energy from the downward-facing LEDs 132 onto the illumination area. The other portions of the system 110 are generally the same as the first system 10, and the reference numerals have been included for a clearer understanding of the arrangement shown.

Figure 5:
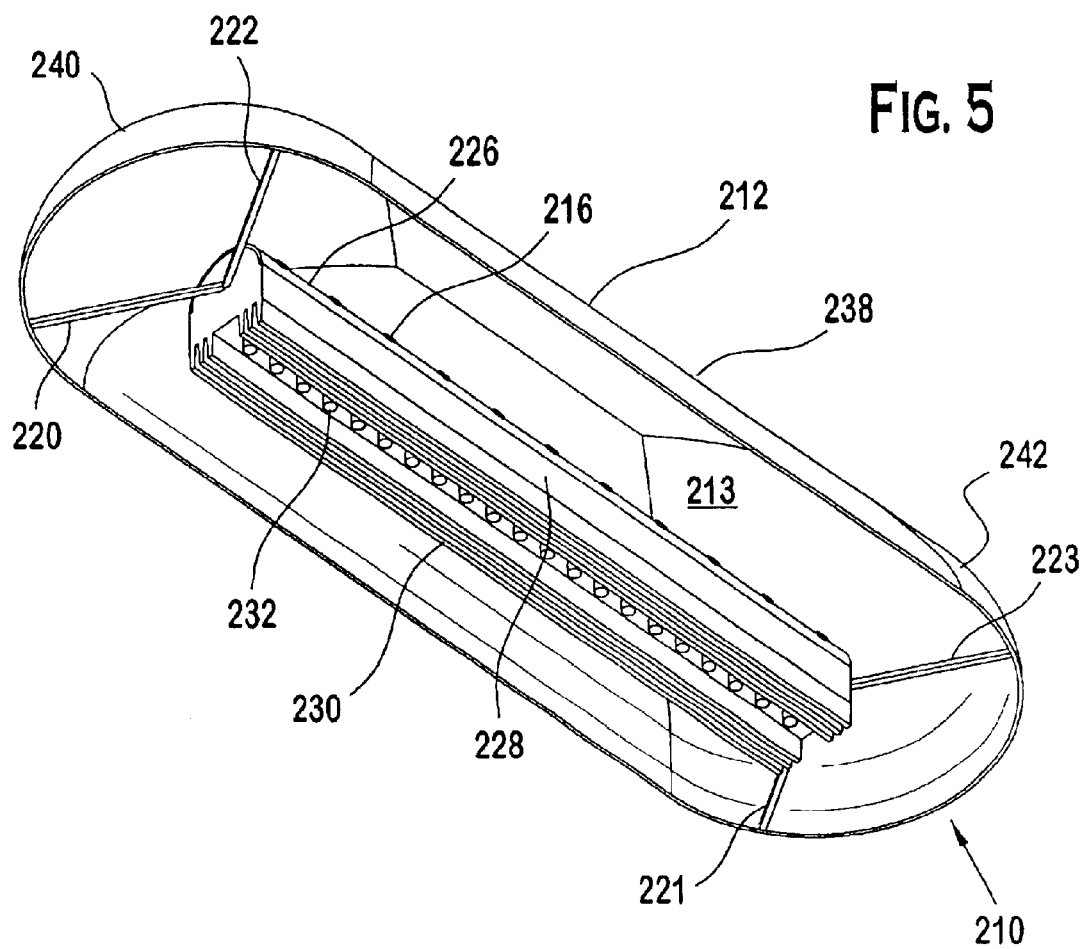
FIG. 5 is a bottom perspective view of a second alternative embodiment of the illumination system of the present invention.

FIG. 5 shows a second alternative to the preferred embodiment of the present invention in which like elements in this embodiment are represented by reference numerals increased by factors of 200. The illumination system 210 includes a core 228, substrate 226, heat sink fins 230 and downward facing LEDs 232 that are similar to that of system 10 (see FIG. 3). In this embodiment, the reflector 212, which is supported by brackets 220, 221, 222, 223, includes a corresponding middle portion 238 that is located between two end portions 240, 242. The middle portion 238 of the reflector 212 is preferably generally elliptical in cross-sectional shape, and the end portions 240, 242 of the reflector 212 close off the open ends with a curved surface whose axes are shaped orthogonal to the primary axis. The design of system 210 captures and reflects light emitted from the LEDs 216 that are located near the ends of the core 228 and redirects the light energy into a usable area (i.e., the illumination area) to increase the efficiency of the system 210.

Figure 6:
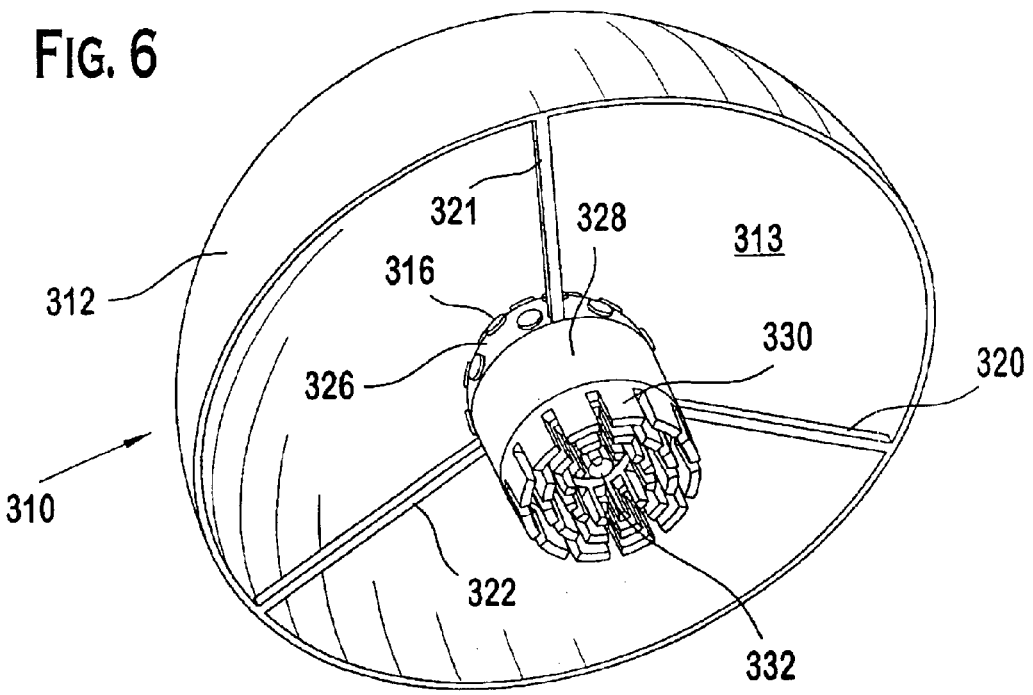
FIG. 6 is a bottom perspective view of a third alternative embodiment of the present invention.

FIG. 6 shows a third alternative embodiment of the present invention in which like elements in this embodiment are represented by reference numerals increased by factors of 300. The illumination system 310 includes a reflector 312 having a reflective surface 313 that is hemispherical in shape. In this embodiment, the LEDs 316 are also surface mounted to a substrate 326 that is generally hemispherical in shape. A lens (not shown) located below the downward-facing LEDs 332 may optionally be included to better focus light energy from the downward-facing LEDs 332 onto the illumination area. Braces 320, 321, 322 are generally used to position the reflector 312. The illumination system 310 is otherwise substantially similar to the illumination system 10 described above and shown in FIGS. 1–3, with the core 328 having cooling fins 330 and optionally including a bottom mounting area for LEDs 332. The illumination system 310 provides an illumination area that is generally circular in shape. Accordingly, the illumination system 310 is best suited for use with certain types of area scanning systems, such as those using area imager based cameras.

While the preferred embodiments of the invention have been described in detail, this invention is not limited to the specific embodiments as described above, which should be considered as merely exemplary. Further modifications and extensions of the present invention may be developed based upon the foregoing, and all such modifications are deemed to be within the scope of the present invention as defined by the appended claims.

What is claimed is:

1. A system for focusing light on an illumination area comprising:

a reflector having a focusing reflective surface and a focal region;

a first light-emitting diode (LED) array comprising a plurality of LEDs located within the focal region, each of the plurality of LEDs of the first LED array being positioned to emit light directly toward the focusing reflective surface; and a second LED array comprising at least one LED positioned to emit light directly toward the illumination area;

wherein the focusing reflective surface reflects light from each of the plurality of LEDs of the first LED array toward the illumination area.

2. The system of claim 1, wherein each of the plurality of LEDs of the first LED array is surface-mounted on a substrate having a generally convex outer surface.

3. The system of claim 2, wherein the substrate comprises a flexible printed circuit board.

4. The system of claim 1, wherein each of the plurality of LEDs of the first LED array is surface-mounted/on a substrate that is secured to a core that dissipates heat.

5. The system of claim 4, wherein the core comprises at least one cooling fin.

6. The system of claim 1, wherein the second LED array comprises a single row of LEDs.

7. The system of claim 1, wherein the focusing reflective surface is concave.

8. The system of claim 7, wherein the focusing reflective surface is generally elliptical.

9. The system of claim 7, wherein the focusing reflective surface is generally parabolic.

10. The system of claim 7, wherein the focusing reflective surface is generally hyperbolic.

11. The system of claim 7, wherein the focusing reflective surface is generally spherical.

12. The system of claim 1, wherein each of the plurality of LEDs of the first light-emitting diode (LED) array includes a zero-power lens.

13. The system of claim 1, wherein the at least one LED of the second LED array includes a focusing lens.

* * * * *